US008298989B2

(12) United States Patent
Funke et al.

(10) Patent No.: US 8,298,989 B2
(45) Date of Patent: Oct. 30, 2012

(54) ACTIVE INGREDIENT COMBINATIONS WITH INSECTICIDAL PROPERTIES

(75) Inventors: Christian Funke, Leichlingen (DE); Rüdiger Fischer, Pulheim (DE); Reiner Fischer, Monheim (DE); Wolfgang Thielert, Odenthal (DE); Anton Kraus, Leichlingen (DE); Heike Hungenberg, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 784 days.

(21) Appl. No.: 12/295,074

(22) PCT Filed: Mar. 28, 2007

(86) PCT No.: PCT/EP2007/002722
§ 371 (c)(1),
(2), (4) Date: Feb. 24, 2009

(87) PCT Pub. No.: WO2007/112893
PCT Pub. Date: Oct. 11, 2007

(65) Prior Publication Data
US 2009/0275471 A1    Nov. 5, 2009

(30) Foreign Application Priority Data

Mar. 30, 2006  (DE) .......................... 10 2006 014 779
Sep. 9, 2006   (DE) .......................... 10 2006 042 437

(51) Int. Cl.
*A01N 25/00* (2006.01)
*A01N 43/40* (2006.01)
*A01N 25/18* (2006.01)

(52) U.S. Cl. ........................................ 504/100; 514/341
(58) Field of Classification Search ................. 504/100; 514/341
See application file for complete search history.

(56) References Cited

U.S. PATENT DOCUMENTS
7,696,232 B2 * 4/2010 Berger et al. ................. 514/341

FOREIGN PATENT DOCUMENTS

| WO | WO 98/35935 | 8/1998 |
| WO | WO 03/074491 | 9/2003 |
| WO | WO 2004/067528 | 8/2004 |
| WO | WO 2004067528 A1 * | 8/2004 |
| WO | WO 2005/107468 | 11/2005 |
| WO | WO2005107468 A * | 11/2005 |
| WO | WO 2005107468 A1 * | 11/2005 |
| WO | WO 2006/023783 | 3/2006 |
| WO | WO 2006/068669 | 6/2006 |
| WO | WO2006068669 A * | 6/2006 |

OTHER PUBLICATIONS

International Search Report, App. No. PCT/EP2007/002722, dated Oct. 31, 2007 (20 pages).

* cited by examiner

*Primary Examiner* — Janet Epps-Smith
*Assistant Examiner* — Courtney Brown
(74) *Attorney, Agent, or Firm* — Baker Donelson Bearman Caldwell & Berkowitz, PC

(57) ABSTRACT

Agrochemical compositions comprising at least one active compound from the class of the anthranilamides and at least one further active compound selected from the group consisting of insecticides, fungicides, and/or acaricides have excellent synergistic activity.

10 Claims, No Drawings

ACTIVE INGREDIENT COMBINATIONS WITH INSECTICIDAL PROPERTIES

CROSS REFERENCE TO RELATED APPLICATIONS

This application is a §371 National Stage Application of PCT/EP2007/002722 filed Mar. 28, 2007 which claims priority from German Application 10 2006 014 779.0 filed Mar. 29, 2006 and German Application 10 2006 042 437.9 filed Sep. 9, 2006.

BACKGROUND OF THE INVENTION

1. Field of the Invention

The present invention relates to synergistic active compound combinations having insecticidal properties comprising at least one active compound from the class of the anthranilamides and at least one further active compound selected from the group consisting of insecticides, fungicides, and acaricides, their preparation and their use for controlling unwanted insects and/or spider mites.

2. Description of Related Art

It is already known that certain compounds from the class of the anthranilamides have insecticidal properties (cf., for example, WO 2004/067528, WO 2006/023783), and insecticidal mixtures of anthranilamides with other pesticides have been described (cf., for example, WO 2005/107468, WO 2006/068669). The content of these publications is expressly incorporated herein by way of reference.

SUMMARY OF THE INVENTION

The activity of these compounds is generally good; however, in specific cases it is unsatisfactory. It has now been found that active compound combinations comprising at least one active compound from the class of the anthranilamides (component A) and at least one further active compound from the class of the insecticides, fungicides or acaricides (component B) do not only have additive, but superadditive synergistic activity.

DETAILED DESCRIPTION OF A PREFFERED EMBODIMENT

Anthranilamides with which such a synergistic effect is achieved on combination with a further active compound are, for example, the known compounds (1) to (22):

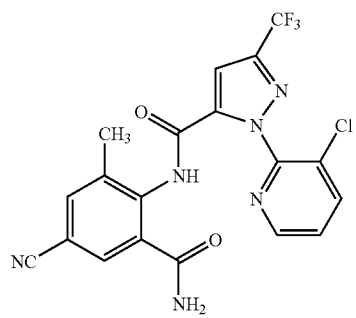
(1)

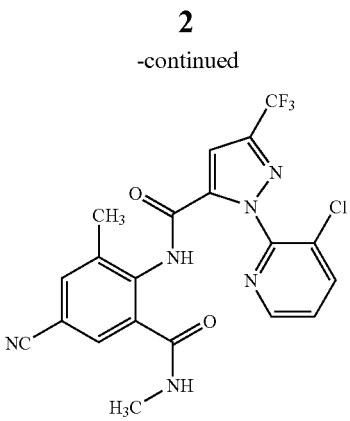
(2)

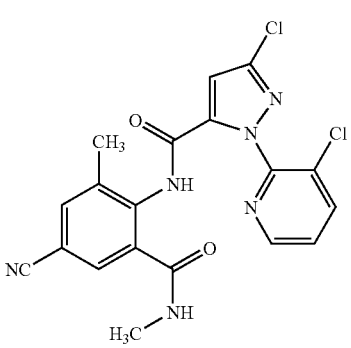
(3)

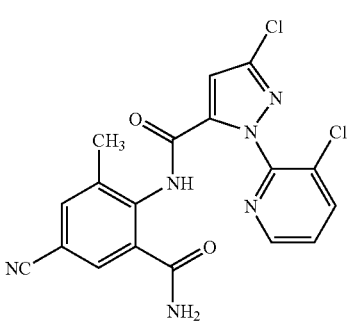
(4)

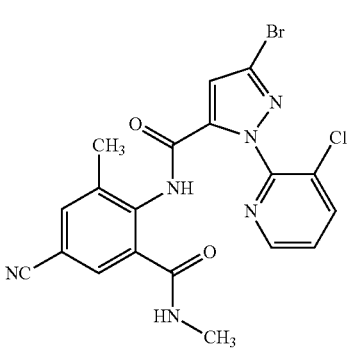
(5)

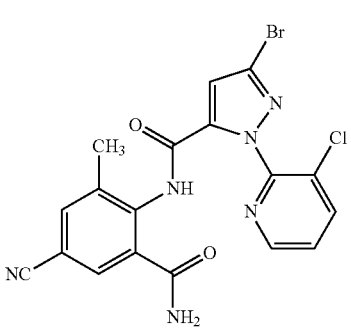
(6)

(7)
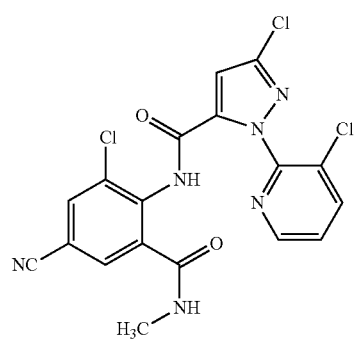
(8)
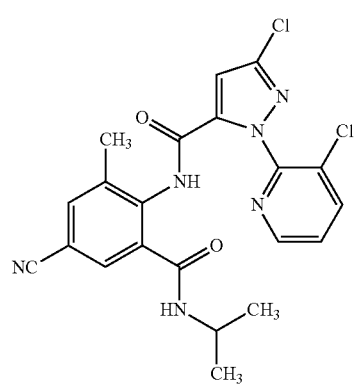
(9)
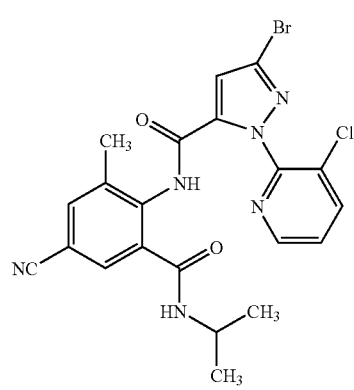
(10)
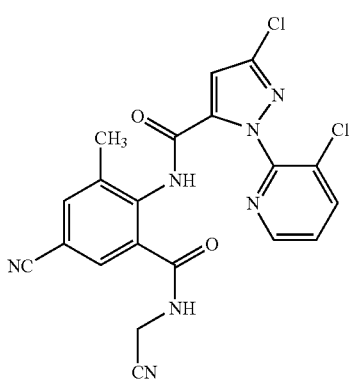
(11)
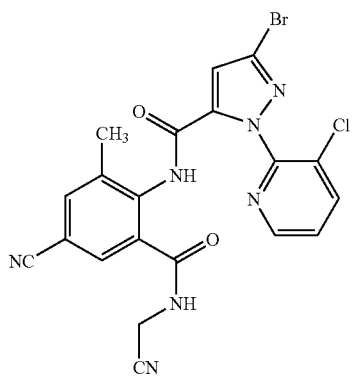
(12)
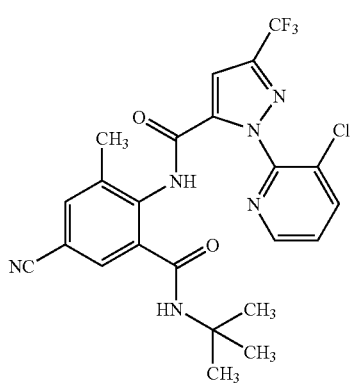
(13)
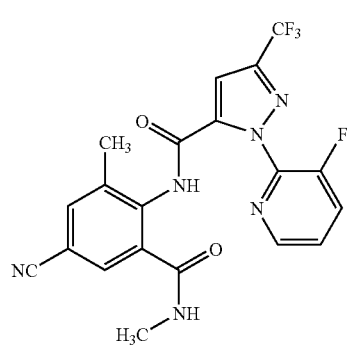
(14)
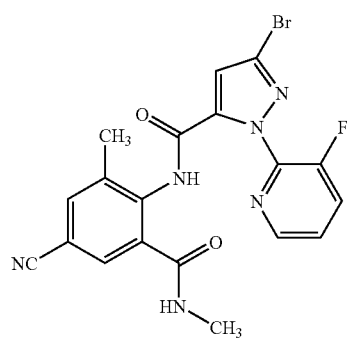

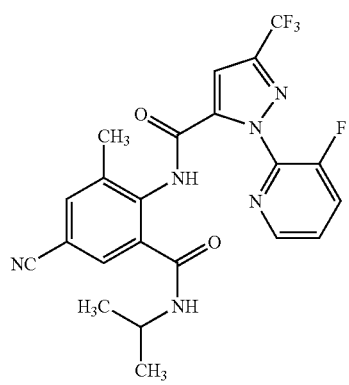
(15)
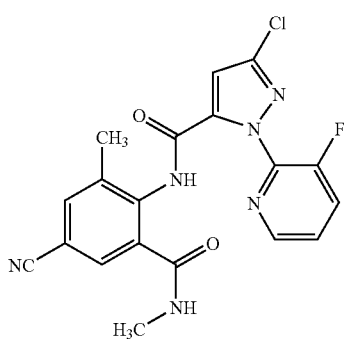
(19)
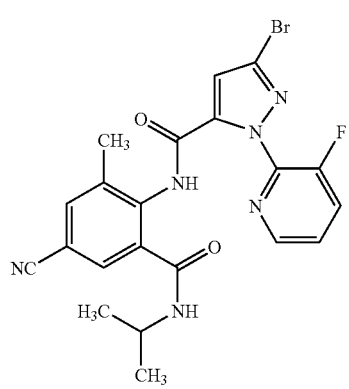
(16)
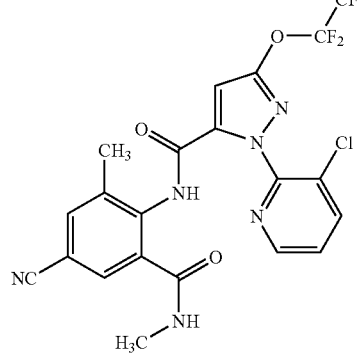
(20)
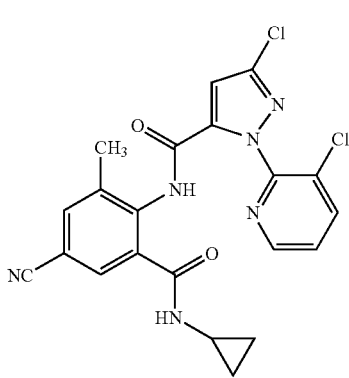
(17)
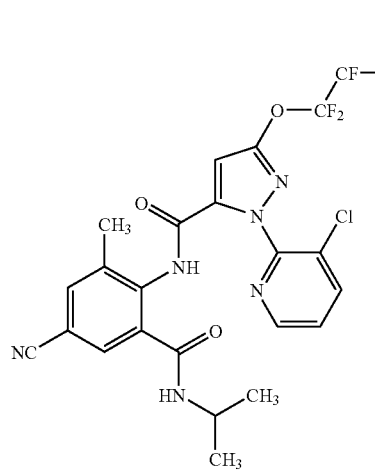
(21)
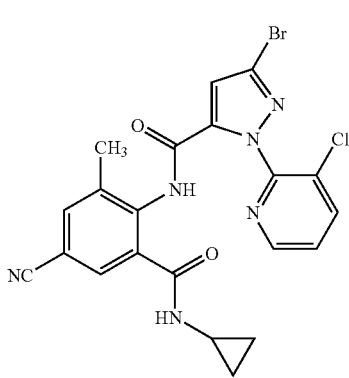
(18)
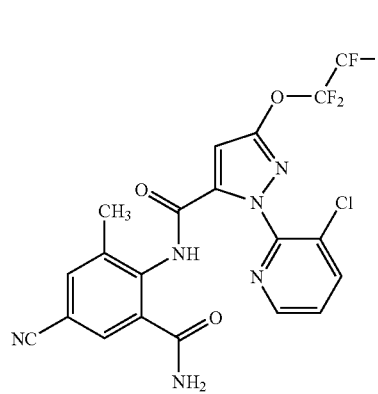
(22)
A preferred embodiment of the subject of the invention are active compound combinations comprising compound (1) as component A and at least one further active compound having insecticidal, acaricidal or fungicidal activity as component B.

A particularly preferred embodiment of the subject of the invention are active compound combinations comprising compound (1) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfnur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (2) as component A and at least one further active compound having insecticidal, acaricidal or fungicidal activity as component B.

A further particularly preferred embodiment of the subject of the invention are active compound combinations comprising compound (2) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (3) as component A and at least one further active compound having insecticidal, acaricidal or fungicidal activity as component B.

A further particularly preferred embodiment of the subject of the invention are active compound combinations comprising compound (3) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifime, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,4-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (4) as component A and at least one further active compound having insecticidal, acaricidal or fungicidal activity as component B.

A further particularly preferred embodiment of the subject of the invention are active compound combinations comprising compound (4) as component A and as component B an active compound selected from the group consisting of
The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (5) as component A and at least one further active compound having insecticidal, acaricidal or fungicidal activity as component B.

A further particularly preferred embodiment of the subject of the invention are active compound combinations comprising compound (5) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (6) as component A and at least one further active compound having insecticidal, acaricidal or fungicidal activity as component B.

A further particularly preferred embodiment of the subject of the invention are active compound combinations comprising compound (6) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (7) as component A and at least one further active compound having insecticidal, acaricidal or fungicidal activity as component B.

A further particularly preferred embodiment of the subject of the invention are active compound combinations comprising compound (7) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, tritriconazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[1-[3(1-fluoro-2-phenylethyl)oxy]phenyl]ethylidene]amino]oxy] methyl]-alpha-(methoxyimino)-N-methyl-alphaE-benzacetamide, N-[2-[3-chloro-5-(trifluoromethyl) pyridin-2-yl]ethyl]-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (8) as component A and at least one further active compound having insecticidal, acaricidal or fungicidal activity as component B.

A further particularly preferred embodiment of the subject of the invention are active compound combinations comprising compound (8) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl]-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (9) as component A and at least one further active compound having insecticidal, acaricidal or fungicidal activity as component B.

A further particularly preferred embodiment of the subject of the invention are active compound combinations comprising compound (9) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (10) as component A and at least one further active compound having insecticidal, acaricidal or fungicidal activity as component B.

A further particularly preferred embodiment of the subject of the invention are active compound combinations comprising compound (10) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (11) as component A and at least one further active compound having insecticidal, acaricidal or fungicidal activity as component B.

A further particularly preferred embodiment of the subject of the invention are active compound combinations comprising compound (11) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (12) as component A and at least one further active compound having insecticidal, acaricidal or fungicidal activity as component B.

A further particularly preferred embodiment of the subject of the invention are active compound combinations comprising compound (12) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (13) as component A and at least one further active compound having insecticidal, acaricidal or fungicidal activity as component B.

A further particularly preferred embodiment of the subject of the invention are active compound combinations comprising compound (13) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (14) as component A and at least one further active compound having insecticidal, acaricidal or fungicidal activity as component B.

A further particularly preferred embodiment of the subject of the invention are active compound combinations comprising compound (14) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfinur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4- chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaEbenzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, metalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (15) as component A and at least one further active compound having insecticidal, acaricidal or fungicidal activity as component B.

A further particularly preferred embodiment of the subject of the invention are active compound combinations comprising compound (15) as component A and as component B an active compound selected from the group consisting of
The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorfolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (16) as component A and at least one further active compound having insecticidal, acaricidal or fungicidal activity as component B.

A further particularly preferred embodiment of the subject of the invention are active compound combinations comprising compound (16) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3- methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (17) as component A and at least one further active compound having insecticidal, acaricidal or fungicidal activity as component B.

A further particularly preferred embodiment of the subject of the invention are active compound combinations comprising compound (17) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (18) as component A and at least one further active compound having insecticidal, acaricidal or fungicidal activity as component B.

A further particularly preferred embodiment of the subject of the invention are active compound combinations comprising compound (18) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-

2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl]-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (19) as component A and at least one further active compound from the class of the insecticides, fungicides or acaricides as component B.

A further particularly preferred embodiment of the subject of the invention are active compound combinations comprising compound (19) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, debacarb, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, 0-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (20) as component A and at least one further active compound having insecticidal, acaricidal or fungicidal activity as component B.

A further particularly preferred embodiment of the subject of the invention are active compound combinations comprising compound (20) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (21) as component A and at least one further active compound having insecticidal, acaricidal or fungicidal activity as component B.

A further particularly preferred embodiment of the subject of the invention are active compound combinations comprising compound (21) as component A and as component B an active compound selected from the group consisting of The Fungicides benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

A further preferred embodiment of the subject of the invention are active compound combinations comprising compound (22) as component A and at least one further active compound having insecticidal, acaricidal or fungicidal activity as component B.

A further particularly preferred embodiment of the subject of the invention are active compound combinations comprising compound (22) as component A and as component B an active compound selected from the group consisting of The Fungicides
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid, benomyl, carbendazim, diethofencarb, fuberidazole, pencycuron, thiabendazole, thiophanate-methyl, zoxamide, diflumetorim, boscalid, carboxin, fenfuram, flutolanil, furametpyr, mepronil, oxycarboxin, penthiopyrad, thifluzamid, azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin, dinocap, fluazinam, fentin acetate, fentin chloride, fentin hydroxide, silthiofam, andoprim, blasticidin-S, cyprodinil, kasugamycin, kasugamycin hydrochloride hydrate, mepanipyrim, pyrimethanil, fenpiclonil, fludioxonil, quinoxyfen, chlozolinate, iprodione, procymidone, vinclozolin, ampropylfos, potassium ampropylfos, edifenphos, iprobenfos (IBP), isoprothiolane, pyrazophos, tolclofos-methyl, biphenyl, iodocarb, propamocarb, propamocarb hydrochloride, fenhexamid, azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine, benthiavalicarb, bialaphos, dimethomorph, flumorph, iprovalicarb, polyoxins, polyoxorim, validamycin A, capropamid, diclocymet, fenoxanil, phthalide, pyroquilon, tricyclazole, acibenzolar-S-methyl, probenazole, tiadinil, captafol, captan, chlorothalonil, copper salts, such as copper hydroxide, copper naphthenate, copper oxychloride, copper sulfate, copper oxide, oxine-copper and Bordeaux mixture, dichlorfluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations comprising calcium polysulfide, thiram, tolylfluanid, zineb, ziram, amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulfate, diphenylamine, ethaboxam, ferimzone, flumetover, flusulfamide, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden -4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)phenyl]ethylidene]amino]oxy]methyl] phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino] methyl]thio]methyl]-.alpha.-(methoxymethylene) benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl) amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N -(3-ethyl-3,5,5-trimethylcyclohexyl)-3-formylamino-2-hydroxybenzamide, 2-[[[[1-[3(1-fluoro-2-phenylethyl)oxy]phenyl]ethylidene]amino]oxy] methyl]-alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3', 4'-dichloro-5-fluorobiphenyl-2-yl)-3-(difluoromethyl)-1-methyl-1H-pyrazole-4-carboxamide, N -(6-methoxy-3-pyridinyl)cyclopropanecarboxamide and 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide, The Insecticides/Acaricides
cyflumetofen, cyenopyrafen, spirotetramat and IKA2002 (O-{(E)-2-(4-chlorophenyl)-2-cyano-1-[2-(trifluoromethyl)phenyl]vinyl}S-methyl thiocarbonate, known from WO 98/35935).

A further fungicide which may be used with preference is N-{2-[1,1'-bi(cyclopropyl)-2-yl]phenyl}-3-(difluoromethyl)-1-methyl-1H-pyrazole-4-carboxamide (known from WO 03/74491).

Fungicides which may be used with particular preference are carbendazim, thiram, carboxim, triticonazole, pyraclostrobin, boscalid, oryzastrobin, azoxystrobin, difluaconazole, fludioxonil, mefenoxan, methalaxyl, benalaxyl, chiralaxyl and N-{2-[1,1'-bi(cyclopropyl)-2-yl]phenyl}-3-(difluoromethyl)-1-methyl-1H-pyrazole-4-carboxamide.

The synergistic effect is particularly pronounced when the active compounds in the active compound combinations according to the invention are present in certain weight ratios. However, the weight ratios of the active compounds in the active compound combinations way be varied within a relatively wide range. In general, the combinations according to the invention comprise one of the active compounds (1) to (22) as component A and a further of the mixing partners according to the invention listed above as component B in the following preferred and particularly preferred mixing ratios:
preferred mixing ratio: 125:1 to 1:125
particularly preferred mixing ratio: 25:1 to 1:25

The mixing ratios are based on weight ratios. The ratio is to be understood as meaning component A:component B The active compound combinations according to the invention, in combination with good plant tolerance and favorable toxicity to warm-blooded animals and good tolerance by the environment, are suitable for protecting plants and plant organs, for increasing the harvest yields, for improving the quality of the harvested material and for controlling animal pests, in particular insects, arachnids, helminths, nematodes and mollusks, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogo-derma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Cameocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

The active compound combinations according to the invention are distinguished in particular by strong action against sucking pests, in particular against *Myzus persicae*, *Aphis gossypii* and *Tetranychus urticae*.

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compound combinations is carried out directly or by allowing the compounds to act on the surroundings, habitat or storage space by the customary treatment methods, for example by immersion, spraying, drenching, evaporation, fogging, scattering, droplet-application, soil injection, painting on, injection and, in the case of propagation material, in particular in the case of seeds, also by applying one or more coats.

The active compound combinations can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or lattices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound combinations according to the invention can be used in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric esters, carbamates, carboxylic esters, chlorinated hydrocarbons, phenylureas, substances produced by microorganisms, inter alia.

A mixture with other known active compounds, such as herbicides, or with fertilizers and growth regulators is also possible.

When used as insecticides, the active compound combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.00000001 to 95% by weight of active compound, preferably between 0.00001 and 1% by weight.

Application is in a manner appropriate for the use forms.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particular advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and snails and slugs by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinothricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated in a particularly advantageous manner with the active compound combinations according to the invention. The preferred ranges stated above for the active compound combinations also apply to the treatment of these plants. Particular emphasis is given to the treatment of plants with the active compound combinations specifically mentioned in the present text.

The active compound combinations according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compound combinations according to the invention.

The active compound combinations according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compound combinations can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the active compound combinations according to the invention have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The active compound combinations according to the invention can likewise be employed for protecting objects which come into contact with saltwater or brackish water, in particular hulls, screens, nets, buildings, moorings and signalling systems, against fouling.

Furthermore, the active compound combinations according to the invention, alone or in combination with other active compounds, may be employed as antifouling agents.

In domestic, hygiene and stored-product protection, the active compound combinations are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The treatment according to the invention of the plants and plant parts with the active compound combinations is carried out either directly or by treating their environment, habitat or storage space by the customary treatment methods, for example by dipping, spraying, drenching vaporizing, misting, broadcasting, droplet application, soil injection, painting on and, in the case of propagation material, in particular seeds, furthermore by coating with one or more layers.

The mixtures according to the invention are particularly suitable for the treatment of seeds. The combinations according to the invention mentioned above as being preferred or particularly preferred may be mentioned as being preferred here. Thus, most of the damage to crop plants which is caused by pests occurs as early as when the seed is infested during storage and after the seed is introduced into the soil, and during and immediately after germination of the plants. This phase is particularly critical since the roots and shoots of the growing plants are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after planting or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also of the germinating plant with a minimum of crop protection products being employed.

The present invention therefore in particular also relates to a method for the protection of seed and germinating plants, from attack by pests, by treating the seed with a composition according to the invention. The invention likewise relates to the use of the compositions according to the invention for the treatment of seed for protecting the seed and the germinating plant from pests. Furthermore, the invention relates to seed which has been treated with a composition according to the invention so as to afford protection from pests.

One of the advantages of the present invention is that the particular systemic properties of the compositions according to the invention mean that treatment of the seed with these compositions not only protects the seed itself, but also the resulting plants after emergence, from pests. In this manner, the immediate treatment of the crop at the time of sowing or shortly thereafter can be dispensed with.

A further advantage is the synergistically increased insecticidal activity of the compositions according to the invention in comparison with the insecticidal individual active compound, which exceeds the expected activity of the two active compounds when applied individually. Advantageous is also the synergistically increased fungicidal activity of the compositions according to the invention in comparison with the fungicidal individual active compound, which exceeds the expected activity of the individually applied active compound. This makes possible an optimization of the amount of active compound employed.

Furthermore, it must be considered as advantageous that the mixtures according to the invention can also be employed in particular in transgenic seed, the plants arising from this seed being capable of expressing a protein directed against pests. By treating such seed with the compositions according to the invention, certain pests can be controlled merely by the expression of the, for example, insecticidal protein, and, in addition, damage prevented by means of the compositions according to the invention.

The compositions according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco potatoes or vegetables (for example tomatoes, cabbages). The compositions according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with a composition according to the invention is also of particular importance. This takes the form of seed of plants which, as a rule, comprise at least one heterologous gene which governs the expression of a polypeptide with particularly insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. and whose gene product shows activity against the European corn borer and/or the corn root worm. It is particularly preferably a heterologous gene derived from *Bacillus thuringiensis*.

Within the scope of the present invention, the composition according to the invention is applied to the seed either alone or in suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The active compound combinations according to the invention comprising at least one fungicide as mixing partner have very good fungicidal properties and can be used for controlling phytopathogenic fungi, such as Plasmodiophoromycetes, Oomycetes, Chytridiomycetes, Zygomycetes, Ascomycetes, Basidiomycetes, Deuteromycetes, etc.

Some pathogens causing fungal diseases which come under the generic names listed above may be mentioned as examples, but not by way of limitation:

Diseases caused by powdery mildew pathogens, such as, for example,
Blumeria species, such as, for example, Blumeria graminis;
Podosphaera species, such as, for example, Podosphaera leucotricha;
Sphaerotheca species, such as, for example, Sphaerotheca fuliginea;
Uncinula species, such as, for example, Uncinula necator;
Diseases caused by rust disease pathogens, such as, for example,
Gymnosporangium species, such as, for example, Gymnosporangium sabinae
Hemileia species, such as, for example, Hemileia vastatrix;
Phakopsora species, such as, for example, Phakopsora pachyrhizi and Phakopsora meibomiae;
Puccinia species, such as, for example, Puccinia recondita or Puccinia triticina;
Uromyces species, such as, for example, Uromyces appendiculatus;
Diseases caused by pathogens from the group of the Oomycetes, such as, for example,
Bremia species, such as, for example, Bremia lactucae;
Peronospora species, such as, for example, Peronospora pisi or P. brassicae;
Phytophthora species, such as, for example Phytophthora infestans;
Plasmopara species, such as, for example, Plasmopara viticola;
Pseudoperonospora species, such as, for example, Pseudoperonospora humuli or Pseudoperonospora cubensis;
Pythium species, such as, for example, Pythium ultimum;
Leaf blotch diseases and leaf wilt diseases caused, for example, by
Alternaria species, such as, for example, Alternaria solani;
Cercospora species, such as, for example, Cercospora beticola;
Cladiosporium species, such as, for example, Cladiosporium cucumerinum;
Cochliobolus species, such as, for example, Cochliobolus sativus
(conidia form: Drechslera, Syn: Helminthosporium);
Colletotrichum species, such as, for example, Colletotrichum lindemuthanium;
Cycloconium species, such as, for example, Cycloconium oleaginum;
Diaporthe species, such as, for example, Diaporthe citri;
Elsinoe species, such as, for example, Elsinoe fawcettii;
Gloeosporium species, such as, for example, Gloeosporium laeticolor;
Glomerella species, such as, for example, Glomerella cingulata;
Guignardia species, such as, for example, Guignardia bidwelli;
Leptosphaeria species, such as, for example, Leptosphaeria maculans;
Magnaporthe species, such as, for example, Magnaporthe grisea;
Mycosphaerella species, such as, for example, Mycosphaerella graminicola;
Phaeosphaeria species, such as, for example, Phaeosphaeria nodorum;
Pyrenophora species, such as, for example, Pyrenophora teres;
Ramularia species, such as, for example, Ramularia collocygni;
Rhynchosporium species, such as, for example, Rhynchosporium secalis;
Septoria species, such as, for example, Septoria apii;
Typhula species, such as, for example, Typhula incamata;
Venturia species, such as, for example, Venturia inaequalis;
Root and stem diseases caused, for example, by
Corticium species, such as, for example, Corticium graminearum;
Fusarium species, such as, for example, Fusarium oxysporum;
Gaeumannomyces species, such as, for example, Gaeumannomyces graminis;
Rhizoctonia species, such as, for example Rhizoctonia solani;
Tapesia species, such as, for example, Tapesia acuformis;
Thielaviopsis species, such as, for example, Thielaviopsis basicola;
Ear and panicle diseases (including maize cobs) caused, for example, by
Alternaria species, such as, for example, Alternaria spp.;
Aspergillus species, such as, for example, Aspergillus flavus;
Cladosporium species, such as, for example, Cladosporium spp.;
Claviceps species, such as, for example, Claviceps purpurea;
Fusarium species, such as, for example, Fusarium culmorum;
Gibberella species, such as, for example, Gibberella zeae;
Monographella species, such as, for example, Monographella nivalis;
Diseases caused by smut fungi, such as, for example,
Sphacelotheca species, such as, for example, Sphacelotheca reiliana;
Tilletia species, such as, for example, Tilletia caries;
Urocystis species, such as, for example, Urocystis occulta;
Ustilago species, such as, for example, Ustilago nuda;
Fruit rot caused, for example, by
Aspergillus species, such as, for example, Aspergillus flavus;
Botrytis species, such as, for example, Botrytis cinerea;
Penicillium species, such as, for example, Penicillium expansum;
Sclerotinia species, such as, for example, Sclerotinia sclerotiorum;
Verticilium species, such as, for example, Verticilium alboatrum;
Seed- and soil-borne rot and wilt diseases, and also diseases of seedlings, caused, for example, by
Fusarium species, such as, for example, Fusarium culmorum;
Phytophthora species, such as, for example, Phytophthora cactorum;
Pythium species, such as, for example, Pythium ultimum;

*Rhizoctonia* species, such as, for example, *Rhizoctonia solani;*
*Sclerotium* species, such as, for example, *Sclerotium rolfsii;*
Cancerous diseases, galls and witches' broom caused, for example, by
*Nectria* species, such as, for example, *Nectria galligena;*
Wilt diseases caused, for example, by
*Monilinia* species, such as, for example, *Monilinia laxa;*
Deformations of leaves, flowers and fruits caused, for example, by
*Taphrina* species, such as, for example, *Taphrina deformans;*
Degenerative diseases of woody plants caused, for example, by
*Esca* species, such as, for example, *Phaemoniella clamydospora;*
Diseases of flowers and seeds caused, for example, by
*Botrytis* species, such as, for example, *Botrytis cinerea;*
Diseases of plant tubers caused, for example, by
*Rhizoctonia* species, such as, for example, *Rhizoctonia solani;*
Diseases caused by bacteriopathogens, such as, for example,
*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora.*

Preference is given to controlling the following diseases of soya beans:
fungal diseases on leaves, stems, pods and seeds caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora Cassiicola*)

Fungal diseases on roots and the stem base caused, for example, by
black root rot (*Calonectria crotalariae*), charcoal rot (*Macrophomina phaseolina*), *fusarium* blight wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

If the compositions according to the invention comprise both at least one insecticidally active compound and at least one fungicidally active compound, both the fungicidal and the insecticidal activity may be enhanced in a superadditive manner.

The expected activity for a given combination of two active compounds can be calculated according to S. R. Colby, Weeds 15 (1967), 20-22) as follows:

If

X is the kill rate, expressed in % of the untreated control, when employing active compound A at an application rate of m g/ha or in a concentration of m ppm, Y is the kill rate, expressed in % of the untreated control, when employing active compound B at an application rate of n g/ha or in a concentration of n ppm and E is the kill rate, expressed in % of the untreated control, when employing active compounds A and B at application rates of m and n g/ha or in a concentration of m and n ppm, then $$E = X + Y - \frac{X \cdot Y}{100}$$

If the actual insecticidal kill rate is higher than the calculated one, the kill rates of the combination are superadditive, i.e. a synergistic effect is present. In this case, the kill rate that is actually observed has to be higher than the value, calculated using the formula above, for the expected kill rate (E).

After the desired period of time, the kill in % is determined. 100% means that all animals have been killed; 0% means that none of the animals have been killed.

USE EXAMPLES

Example A

| *Aphis gossypii* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The determined kill rates are entered into Colby's formula (see page 71).

In this test, for example, the following combinations of active compounds according to the present application show a synergistically enhanced activity compared to the active compounds applied on their own:

TABLE A

Plant-damaging insects
*Aphis gossypii* test

| Active compounds | Active compound concentration in ppm | Kill rate in % after 6$^d$ found* | calc.** |
|---|---|---|---|
| (5) [structure: bromopyrazole carboxamide with methyl, cyano-phenyl, N-methylamide, chloropyridine] | 0.8 | 45 | |
| spirotetramat | 4 | 15 | |
| cyflumetofen | 0.16 | 0 | |
| (5) + spirotetramat (1:5) | 0.8 + 4 | 90 | 53.25 |
| (5) + cyflumetofen (5:1) | 0.8 + 0.16 | 75 | 45 |

*found = activity found
**calc. = activity calculated using Colby's formula

Example B

*Myzus persicae* test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed. The determined kill rates are entered into Colby's formula (see page 71).

In this test, for example, the following combinations of active compounds according to the present application show a synergistically enhanced activity compared to the active compounds applied on their own:

TABLE B

| | Plant-damaging insects *Myzus persicae* test | | |
|---|---|---|---|
| Active compounds | Active compound concentration in ppm | Kill rate in % after 1$^d$ found* | calc.** |
| 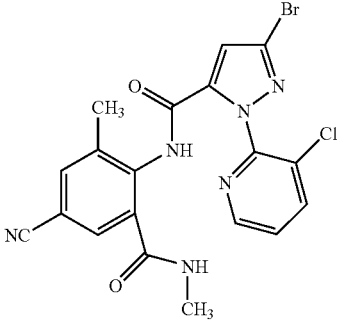 | 4 | 10 | |
| 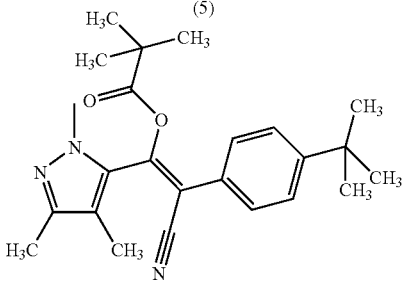 cyenopyrafen | 4 | 0 | |
| (5) + cyenopyrafen (1:1) | 4 + 4 | 50 | 10 |
| 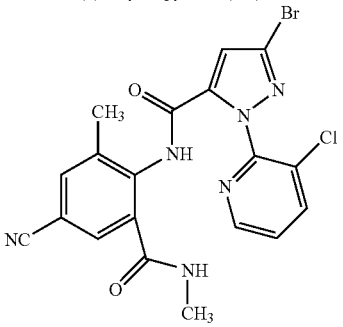 (5) | 0.16 | 5 | |
| 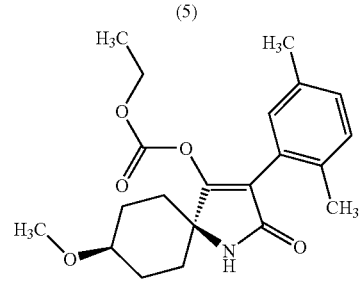 spirotetramat | 0.8 | 10 | |
| (5) + spirotetramat (1:5) | 0.16 + 0.8 | 45 | 14.5 |

*found = activity found
**calc. = activity calculated using Colby's formula

Example C

Tetranychus urticae test (OP-resistent, dip application)

| Solvent: | 7 parts by weight of dimethylformamide |
|---|---|
| Emulgator: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Bush beans (*Phaseolus vulgaris*) heavily infested by the Greenhouse red spider mite (*Tetranychus urticae*) are dipped into a preparation of active compound of the desired concentration.

After the desired period of time, the kill in % is determined. 100% means that all spider mites have been killed; 0% means that none of the spider mites have been killed.

In this test, the following combination of active compounds according to the present application showed a synergistically enhanced activity compared to the active compounds applied on their own:

TABLE C

Plant-damaging acarines
*Tetranychus urticae* test

| Active compounds | Active compound concentration in ppm | Kill rate in % after 7$^d$ found* | calc.** |
|---|---|---|---|
| (5) | 0.16 | 0 | |
| spirotetramat | 0.8 | 25 | |
| (5) + spirotetramat (1:5) | 0.16 + 0.8 | 90 | 25 |

*found = activity found
**calc. = activity calculated using Colby's formula

The invention claimed is:

1. An agrochemical composition comprising an anthranilamide of the following formula:

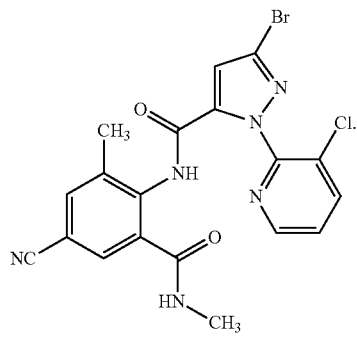

and at least one further active compound selected from the group consisting of cyflumetofen, cyenopyrafen and spirotetramat.

2. A method for controlling an animal pest comprising treating an animal pest and/or a habitat thereof with a composition of claim 1.

3. A method of claim 2 wherein said composition is allowed to act on animal pests and/or a habitat thereof and/or seed.

4. A process for preparing agrochemical compositions comprising mixing a composition of claim 1 with an extender and/or surfactant.

5. A composition according to claim 1 for treating seed, for treating a transgenic plant, and/or for treating seed of a transgenic plant.

6. Seed treated with a composition as claimed in claim 5.

7. An agrochemical composition of claim 1, wherein said at least one further active compound is cyflumetofen.

8. An agrochemical composition of claim 1, wherein said at least one further active compound is cyenopyrafen.

9. An agrochemical composition of claim 1, wherein said at least one further active compound is spirotetramat.

10. An agrochemical composition of claim 1, wherein said at least one anthranilamide and said at least one further active compound are present in a weight ratio ranging from 25:1 to 1:25.

* * * * *